United States Patent [19]

Szweda et al.

[11] Patent Number: 5,667,770
[45] Date of Patent: Sep. 16, 1997

[54] LONG WEARING LIPSTICK

[75] Inventors: John Anthony Szweda, River Vale, N.J.; Celeste Anne Lutrario, Hamden, Conn.

[73] Assignee: Elizabeth Arden Company, Division of Conopco, Inc., New York, N.Y.

[21] Appl. No.: 622,503

[22] Filed: Mar. 25, 1996

[51] Int. Cl.⁶ .......................... A61K 7/04; A61K 7/025
[52] U.S. Cl. .................. 424/64; 424/61; 424/401
[58] Field of Search ...................... 424/61, 63, 64, 424/401

[56] References Cited

U.S. PATENT DOCUMENTS

| | | | |
|---|---|---|---|
| 5,085,856 | 2/1992 | Dunphy | 424/64 |
| 5,108,737 | 4/1992 | Dunphy | 424/64 |
| 5,225,186 | 7/1993 | Castrogiovanni et al. | 424/64 |
| 5,310,547 | 5/1994 | Dunphy | 424/64 |
| 5,368,857 | 11/1994 | Corcoran et al. | 424/401 |

OTHER PUBLICATIONS

*Soap/cosmetics/Chemical Specialties*, Jan. 1995—Guerlain Kisskiss Long–Lasting Lipstick.
*Happi*, Nov. 1995—Lancome LipColour.
Magazine Advertisement 1995—Ellen Betrix.

*Primary Examiner*—Thurman K. Page
*Assistant Examiner*—Sharon Howard
*Attorney, Agent, or Firm*—Milton L. Honig

[57] ABSTRACT

A lipstick is provided formulated to include a wax and a phytosphingosine type ceramide. The ceramide improves wearability of the lipstick. Wearability may be further improved through inclusion of a polyamide resin which also achieves increase in gloss/shine.

8 Claims, No Drawings

LONG WEARING LIPSTICK

BACKGROUND OF THE INVENTION

1. Field of the Invention

The invention relates to a long wearing lipstick, especially a lipstick also exhibiting excellent gloss properties.

2. The Related Art

Quality lipsticks are judged by a variety of characteristics. These include extended wearability, glossiness, moisturization, non-smearing, non-bleeding and texture properties. Certain of these properties may be mutually exclusive. Additives that contribute to wearability may interfere with glossiness or moisturization.

About three years ago, the Elizabeth Arden Company introduced a line of lipstick products under the LipSpa® brand. These lipsticks were specially formulated to contain water, the concept being to introduce glycerol and other normally wax insoluble ingredients directly to the lips. U.S. Pat. Nos. 5,310,547, 5,108,737 and 5,085,856 all to Dunphy et al. describe this technology.

In January 1995, Guerlain introduced a long-lasting lipstick under the Kisskiss brand. The formulation was said to contain ceramides, panthenol, a plant gum and resin complex and a sun filter to help moisturize and protect lips while offering a long-lasting matte finish. Ellen Betric, a German company, launched Brilliant Lipstick in 1995 advertising the product to have "staying power and care". Lancome followed with a product branded Rouge Sensation Multi-Sensation Lipcolour with moisturizing properties. Both the Ellen Betrix and Lancome formulations were advertised to include ceramides.

Ceramides represents an important group of lipids, members of which are found in the epidermis of mammals. Skin ceramides are believed to play an important role in water permeability properties, providing an epidermal water-barrier functioning to give increased strength to skin structure and to decrease water loss. Ceramides are N-acylated sphingosine bases. Sphingosine bases are of variable chain length and have the general formula (1):

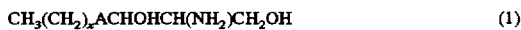

$$CH_3(CH_2)_xACHOHCH(NH_2)CH_2OH \quad (1)$$

where A is —CH=CH— (sphingosine), —CH$_2$—CHOH— (phytosphingosine) or —CH$_2$CH$_2$— (dihydrosphingosine), and where x is generally in the broad range 7 to 27, more typically in the range 10 to 16. Seven distinguishable groups of ceramides have been identified in pig and human epidermis. Each group consists of molecules of varying fatty acid chain length.

Although the aforementioned lipsticks have filled certain consumer needs with their new technology, there still is demand for improved products. Most especially, there is a need for a long wearing lipstick which does not sacrifice the characteristic of high glossiness, combined with good moisturization.

Accordingly, it is an object of the present invention to provide a long wearing lipstick.

Another object of the present invention is to provide a lipstick that combines long wear with high glossiness.

Still another object of the present invention is to provide a lipstick of long wear and high glossiness which is also moisturizing, non-smearing, non-bleeding, cream finished and has a lightweight feel on the lips.

These and other objects, features and advantages of the present invention will become more readily apparent through consideration of the following summary, detailed description and examples which follow.

SUMMARY OF THE INVENTION

A lipstick of long wear is provided which includes:

(i) from 1 to 99% of a wax; and (ii) from 0.00001 to 1% of a phytosphingosine type ceramide having

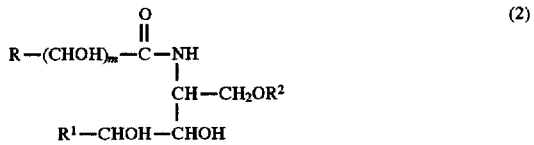

wherein:

R represents a linear or branched, saturated or unsaturated, hydroxylated or non-hydroxylated aliphatic hydrocarbon group having from 1 to 49 carbon atoms or a subgroup (3):

$$Y-O-(C_aH_b)- \quad (3)$$

R$^1$ represents a linear or branched, saturated or unsaturated, hydroxylated or non-hydroxylated aliphatic hydrocarbon group having from 8 to 28 carbon atoms;

R$^2$ represents H, a phosphate, a sulfate or a sugar;

a is an integer of from 7 to 50;

b is an integer of from 10 to 100;

m is 0 or 1;

Y represents H or a C$_{14}$–C$_{22}$ fatty acid having general structure (4):

wherein:

z is —OH or an epoxy oxygen;

x is an integer of from 12 to 20;

y is an integer of from 20 to 40; and z is 0 or an integer of from 1 to 4.

DETAILED DESCRIPTION OF THE INVENTION

Now it has been discovered that a certain type of ceramide of the phytosphingosine variety when incorporated into a lipstick base imparts a substantial increase in long lasting wear yet has no adverse affect upon glossiness.

The phytosphingosine type ceramide of the present invention has the general structure (2):

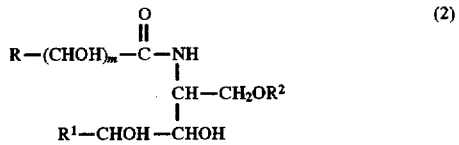

wherein R represents a linear or branched saturated or unsaturated, hydroxylated or non-hydroxylated aliphatic hydrocarbon group having from 1 to 49 carbon atoms or a subgroup (3):

$$Y-O-(C_aH_b)- \quad (3)$$

$R^1$ represents a linear or branched, saturated or unsaturated, hydroxylated or non-hydroxylated aliphatic hydrocarbon group having from 8 to 28 carbon atoms;

$R^2$ represents H, a phosphate, a sulfate or a sugar:
a is an integer of from 7 to 50;
b is an integer of from 10 to 100;
m is 0 or 1;

Y represents H or a $C_{14}$–$C_{22}$ fatty acid having general structure (4):

$$\overset{O}{\underset{\|}{-C}}-(C_xH_yZ_z)CH_3 \quad (4)$$

wherein:
z is —OH or an epoxy oxygen;
x is an integer of from 12 to 20;
y is an integer of from 20 to 40; and
z is 0 or an integer of from 1 to 4.

With reference to structure (2), the group R preferably represents an aliphatic hydrocarbon group having from 12 to 30 carbon atoms or the group Y—O—$(C_aH_b)$—; while the group $R^1$ preferably represents an aliphatic hydrocarbon group having from 12 to 22 carbon atoms.

With reference to structure (3), the value of "a" is preferably an integer of from 24 to 30 and the value of "b" is preferably an integer of from 44 to 60.

Also, with reference to structure (3), the group Y preferably represents a straight chain saturated $C_{16}$–$C_{18}$, fatty acid or a straight chain all cis n-6,9 di-unsaturated $C_{16}$–$C_{18}$ fatty acid.

Specific examples of these phytosphingosine-containing ceramides are those having the structures (5) to (17):

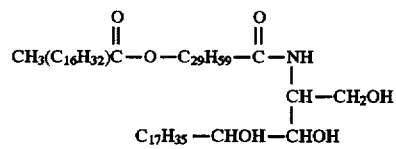  (5)

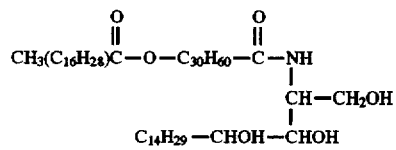  (6)

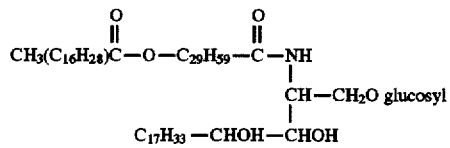  (7)

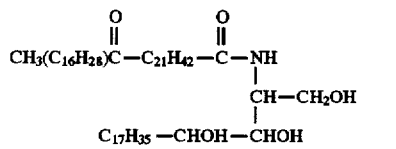  (8)

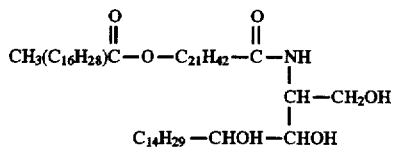  (9)

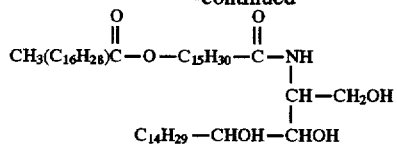  (10)

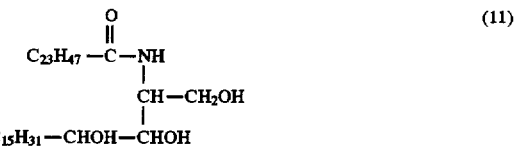  (11)

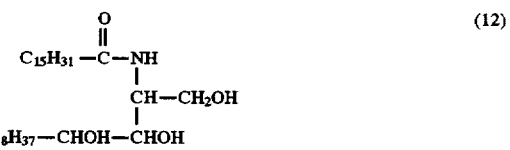  (12)

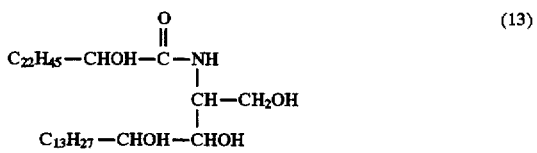  (13)

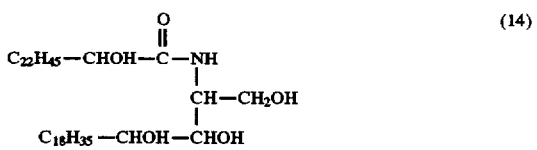  (14)

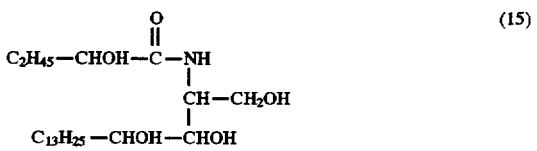  (15)

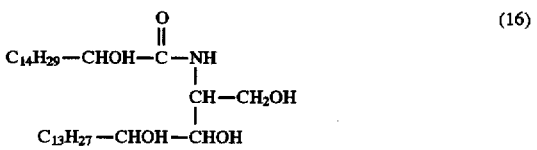  (16)

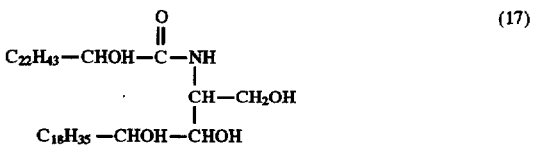  (17)

The amount of the phytosphingosine type ceramide present in compositions according to the invention is from 0.00001 to 1%, preferably from 0.10 to 0.8%, more preferably from 0.20 to 0.5%, optimally from 0.2 to 0.3% by weight.

The most preferred phytosphingosine is Ceramide 3, especially Ceramide 3B referred to as N-oleoyl-phytosphingosine.

A wax will also be present in compositions of the invention. Waxes are low-melting organic compounds or mixtures of high molecular weight substances. They are solid at room temperature (20° C.) and are generally similar in composition to fats and oils, except that they contain no glycerides. Some are hydrocarbons; others are esters of fatty acids and alcohols. Waxes are thermoplastic, but since they are not high polymers, they are not considered in the family of plastics. Natural, mineral and synthetic waxes may all be employed. Among the natural waxes are those of animal origin (beeswax, spermaceti, lanolin, shellac wax), vegetable (carnauba, candelilla, bayberry, sugarcane wax) and mineral (ozokerite, ceresin, montan, paraffin, microcrystalline, petroleum and petrolatum wax). Synthetic waxes include polyol ether-esters such as "carbowax", hydrogenated castor oil and hydrocarbon-type waxes.

Most preferred are candelilla, ozokerite, carnauba, beeswax, lanolin and spermaceti waxes.

Amounts of the wax may range anywhere from about 1 to about 99% by weight, preferably from about 5 to about 50%, optimally from about 10 to about 30% by weight.

Another aspect of the present invention is the inclusion of a thermoplastic resin, particularly a polyamide, the resin should have a softening point per ASTM E-28 ranging from 80° to 180° C., preferably from 100° to 120° C. Viscosity of the resin should at 160° C. range from 0.2 to 300, preferably from 1 to 35, most preferably from 20 to 30 poise (Brookfield Viscometer, Thermosel). Illustrative of the resins are polyamides available under the Versamide trademark from the Henkel Corporation, Ambler, Pa. Most preferred is Versamide® 930. Amounts of the resin in lipsticks of the present invention will range from about 0.1 to about 10%, preferably from 0.3 to 5%, optimally from 0.5 to 1.5% by weight.

Powders insoluble in hydrocarbon waxes may also be included as components of lipsticks according to the present invention. Powders will usually have a melting point in excess of 20° C. These powders may either be organic or inorganic. Among the inorganic materials are clays (e.g. kaolin), mica, talc, sodium bicarbonate, silica and boron nitride. These materials may be uncoated or coated, titanium dioxide coated mica being one example. Illustrative organic powders include modified starches (e.g. aluminum starch octenylsuccinate sold as Dry Flo®) and polymers (e.g. nylon and polyethylene). Particle size for the powders may range from 0.01 to 100 microns, preferably from 0.1 to 30 microns average particle size diameter. Amounts of the powders may range from 0.1 to 50%, preferably from 1 to 30%, optimally from 5 to 15% by weight.

Lipsticks of the present invention are usually opaque but may also be transparent or at least translucent.

Whether opaque or transparent/translucent, the lipsticks will in most instances contain a colorant. Amounts of colorant will range from about 0.1 to about 40%, preferably from 1 to 30%, optimally from 15 to 25% by weight.

Colorants may either be organic, inorganic or combinations (e.g. metallic salts of organic bases). Typical inorganic colorants include titanium dioxide, zinc oxide, iron oxide, bismuth oxychloride, cobalt and aluminum salts. Organic colorants are usually water-soluble dyes examples of which include Red 3, Red 7, Red 21, Red 27, Red 28, Red 33, Yellow 5, Yellow 6, Yellow 10, Orange 5 and Blue 1. When the dyes are precipitated onto an absorptive surface such as alumina hydrate, materials known as aluminum lakes form. These lakes are often utilized for lipsticks.

Emollient oils may also be included in lipsticks of the present invention. Emollient oils which are defined as oily organic substances liquid at room temperature (i.e. 20° C.) can be employed singly or as mixtures of two or more oils. They normally will be present at levels from about 2 to about 85%, preferably from about 30 to 70% by weight of the composition.

These oils are useful not only for emollient purposes but may also impart viscosity, tackiness and drag properties. Examples of suitable oils include caprylic triglycerides; capric triglycerides; isostearic triglycerides; adipic triglycerides; propylene glycol myristyl acetate; lanolin oil; polybutene; isopropyl palmitate; isopropyl myristate; pentaerythritol caprate; diethyl sebacate; diisopropyl adipate; hexadecyl stearate; cetyl oleate; oleyl alcohol; hexadecyl alcohol; octyl dodecanol; wheatgerm oil; hydrogenated vegetable oils; petrolatum; modified lanolins; branched-chain hydrocarbons; alcohols and esters; castor oil; corn oil; sunflowerseed oil; cottonseed oil; olive oil; palm kernel oil; rapeseed oil; safflower seed oil; jojoba oil; wheatgerm oil; evening primrose oil; avocado oil; mineral oil; and volatile and nonvolatile silicone oils.

The following examples will more fully illustrate certain aspects of the present invention. All parts, percentages and proportions referred to herein and in the appended claims are by weight unless otherwise indicated.

EXAMPLE 1

A lipstick according to the present invention was formulated containing the following ingredients.

| INGREDIENT | WEIGHT % |
| --- | --- |
| Luxury Matte Base | 26.93 |
| Red #6 | 14.79 |
| Ceraphyll 847 ® | 10.00 |
| Al Starch Octenylsuccinate | 5.77 |
| Kaolin | 5.72 |
| Castor Oil | 5.43 |
| Red #7 | 5.24 |
| Nylon | 5.00 |
| Yellow #5 | 4.56 |
| Candelilla Wax | 4.00 |
| Oleyl Alcohol | 4.00 |
| Silk Mica | 2.06 |
| Silicone Fluid | 2.00 |
| Ozokerite | 1.00 |
| Supermol S ® | 1.00 |
| Timica Brilliant Gold ® | 1.00 |
| Versamid 930 | 1.00 |
| Red #27 | 0.30 |
| Ceramide 3B | 0.20 |
| Orgasol 2002D ® | |

EXAMPLE 2

Another lipstick according to the present invention can be formulated containing the following ingredients.

| INGREDIENT | WEIGHT % |
| --- | --- |
| Castor Oil | 32.73 |
| Red #27 | 14.90 |
| Ozokerite Wax | 8.95 |
| Polyglycerol Polyester Mixture | 8.61 |
| Octyl Dodecanol | 5.81 |
| Caprylic/Capric/Isostearic/Adipic Triglycerides Mixture | 5.81 |
| Titanium Dioxide Coated Mica | 4.90 |
| Carnauba Wax | 3.97 |
| Candelilla Wax | 3.97 |
| Hydrogenated Castor Oil | 3.88 |
| Ultramarine Blue | 3.76 |
| Microcrystalline Wax | 2.40 |
| Ceramide 3B | 0.20 |
| Propyl p-hydroxybenzoate | 0.09 |
| Butylated Hydroxyanisole | 0.02 |

EXAMPLE 3

A set of clinical experiments were conducted to evaluate the effect of various ceramides and other materials on wear and gloss/shine properties. The lipsticks tested had formulas A through F listed in the Table below.

| INGREDIENT | CONTROL | A | B | C | D | E | F |
|---|---|---|---|---|---|---|---|
| Castor Oil | 14.41 | 14.31 | 14.21 | 13.98 | 13.81 | 13.21 | 12.21 |
| Red #7 | 8.00 | 8.00 | 8.00 | 8.00 | 8.00 | 8.00 | 8.00 |
| Red Oxide | 8.00 | 8.00 | 8.00 | 8.00 | 8.00 | 8.00 | 8.00 |
| Isosteareth-2 | 8.00 | 8.00 | 8.00 | 8.00 | 8.00 | 8.00 | 8.00 |
| Candelilla Wax | 6.50 | 6.50 | 6.50 | 6.50 | 6.50 | 6.50 | 6.50 |
| Aluminum Starch | 5.77 | 5.77 | 5.77 | 5.77 | 5.77 | 5.77 | 5.77 |
| Kaolin | 5.72 | 5.72 | 5.72 | 5.72 | 5.72 | 5.72 | 5.72 |
| Orgasol ® | 5.04 | 5.04 | 5.04 | 5.04 | 5.04 | 5.04 | 5.04 |
| Cetearyl Octanoate | 5.00 | 5.00 | 5.00 | 5.00 | 5.00 | 5.00 | 5.00 |
| Isodecyl Neopentanoate | 4.50 | 4.50 | 4.50 | 4.50 | 4.50 | 4.50 | 4.50 |
| Red #6 | 4.00 | 4.00 | 4.00 | 4.00 | 4.00 | 4.00 | 4.00 |
| Silk Mica | 3.06 | 3.06 | 3.06 | 2.06 | 3.06 | 3.06 | 3.06 |
| Myristyl Lactate | 3.00 | 3.00 | 3.00 | 3.00 | 3.00 | 3.00 | 3.00 |
| C18–C36 Acid Triglyceride | 2.80 | 2.80 | 2.80 | 2.80 | 2.80 | 2.80 | 2.80 |
| Sunflower Monoglyceride | 2.80 | 2.80 | 2.80 | 2.80 | 2.80 | 2.80 | 2.80 |
| Ozokerite | 2.50 | 2.50 | 2.50 | 2.50 | 2.50 | 2.50 | 2.50 |
| Silicone Fluid | 2.00 | 2.00 | 2.00 | 2.00 | 2.00 | 2.00 | 2.00 |
| Ozokerite | 2.00 | 2.00 | 2.00 | 2.00 | 2.00 | 2.00 | 2.00 |
| Apricot Kernel Oil | 0.40 | 0.40 | 0.40 | 0.40 | 0.40 | 0.40 | 0.40 |
| Ceramide 3B | 0.00 | 0.10 | 0.20 | 0.50 | 0.20 | 0.20 | 0.20 |
| Versamid ® 930 | 0.00 | 0.00 | 0.00 | 0.00 | 0.50 | 1.00 | 2.00 |
| Total | 100.00 | 100.00 | 100.00 | 100.00 | 100.00 | 100.00 | 100.00 |

The clinical evaluation involved five (5) women in a one day use test. Panelists applied the test product and the Control each to half their lip. Thus, one product was worn on the left side and the other on the right side of the lips. After intervals of approximately thirty minutes each, the lipsticks were evaluated for wear and gloss/shine. These properties were rated on a scale from 0 to 3, with 0 being no improvement and 3 constituting considerable improvement (i.e. less wear and better gloss/shine). Results are outlined below.

| FORMULA | GLOSS/SHINE | WEAR |
|---|---|---|
| Control | 0 | 0 |
| A | 0 | 0 |
| B | 0 | 1 |
| C | 0 | 1 |
| D | 1 | 2 |
| E | 2 | 2 |
| F | 2 | 2 |

No visible difference was seen between the Control and formula A (with 0.1% of Ceramide 3B). Improved wear was evident as the amount of Ceramide 3B increased as shown with formulas B and C incorporating 0.2 and 0.5%, respectively.

Inclusion of Versamid® 930 (polyamide resin) provided a substantial improvement in wear. See formulas D, E and F. Gloss/shine also markedly improved in the presence of Versamid® 930.

Attempts were unsuccessful to incorporate Ceramide 1 into the Control formula at levels of even 0.1%. Ceramide 1 is N-(w-octadecanoyloxyheptacosanoyl)phytosphingosine.

The foregoing description and examples illustrate selected embodiments of the present invention. In light thereof, various modifications will be suggested to one skilled in the art, all of which are within the spirit and purview of this invention.

What is claimed is:

1. A lipstick comprising:

(i) from 1 to 99% by weight of a wax; and (ii) from 0.00001 to 1% by weight of N-oleoyl-phytosphingosine.

2. The lipstick according to claim 1 further comprising from 0.1 to 50% of a powder insoluble in hydrocarbon wax.

3. The lipstick according to claim 1 further comprising from 0.1 to 10% by weight of a polyamide resin.

4. The lipstick according to claim 3 wherein the resin is present in an amount from 0.8 to 1.5% by weight.

5. The lipstick according to claim 1 wherein the N-oleoyl-phytosphingosine is present in an amount from 0.2 to 0.5% by weight.

6. The lipstick according to claim 1 further comprising from 0.1 to 40% of a colorant.

7. The lipstick according to claim 1 further comprising from 2 to 85% of an emollient oil.

8. The lipstick according to claim 1 wherein the wax is selected from the group consisting of candelilla, ozokerite, carnauba, beeswax, lanolin, spermaceti and wax combinations thereof.

* * * * *